(12) United States Patent
Weber et al.

(10) Patent No.: US 6,424,413 B1
(45) Date of Patent: *Jul. 23, 2002

(54) MULTI-CHANNEL INTEGRATING SPHERE

(75) Inventors: William L. Weber; Harold R. Van Aken, both of Wallkill; Perry A. Palumbo, Gardiner; Joseph Corrado, Marlboro, all of NY (US)

(73) Assignee: GretagMacbeth LLC, New Windsor, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/097,312

(22) Filed: Jun. 12, 1998

(51) Int. Cl.$^7$ .................................................. G01J 1/04
(52) U.S. Cl. ........................ 356/236; 356/319; 250/228
(58) Field of Search ................................. 356/236, 319, 356/416, 418, 419, 445, 446, 323, 325, 326, 328; 250/228; 359/707–711

(56) References Cited

U.S. PATENT DOCUMENTS

| | | | |
|---|---|---|---|
| 3,998,551 A | * | 12/1976 | Suga |
| 4,232,971 A | * | 11/1980 | Suga |
| 4,310,246 A | * | 1/1982 | Blazek |
| 4,487,504 A | * | 12/1984 | Goldsmith |
| 4,583,860 A | * | 4/1986 | Butner |
| 4,663,522 A | * | 5/1987 | Welbourn et al. |
| 4,673,818 A | * | 6/1987 | Guerra |
| 4,881,811 A | * | 11/1989 | O'Brien |
| 4,900,923 A | * | 2/1990 | Gerlinger ............... 356/236 |
| 4,921,351 A | * | 5/1990 | Kohigashi et al. |
| 4,932,779 A | * | 6/1990 | Keane .................... 356/236 |
| 4,968,143 A | * | 11/1990 | Weston |
| 4,995,727 A | * | 2/1991 | Kawagoe et al. |

(List continued on next page.)

FOREIGN PATENT DOCUMENTS

| | | | |
|---|---|---|---|
| DE | 4423698 | * | 1/1996 |
| WO | WO 82 01767 A | | 5/1982 |
| WO | WO 85 37761 A | | 11/1996 |

OTHER PUBLICATIONS

Publication of CIE No. 15.2 "Colorimetry" Second Edition 1986.*

Product Brochure: SPECTRO/plus Spectrophotometer, Coloar and Appearance Technology, Inc. Princeton, NJ.*

ASTM Standard D523–85, ASTM Standards on Color and Appearance Measurement, $2^{nd}$ ed. (1987).*

(List continued on next page.)

*Primary Examiner*—Hoa Q. Pham
(74) *Attorney, Agent, or Firm*—Morgan & Finnegan, L.L.P.

(57) ABSTRACT

An integrating sphere, and an integrating sphere-based reflectance colorimeter/spectrophotometer for the measurement of color and appearance, having multiple receivers capable of concurrently receiving optical radiation scattered/reflected from a diffusely illuminated sample surface, with the capability of multiple measurement modes (e.g., multiple specular component excluded (SCE), SCE and specular component included (SCI), multiple SCI), multiple areas-of-view for a given measurement mode, multiple viewing angles per measurement mode, and combinations thereof. An embodiment of the invention includes two SCI receivers and two SCE receivers, each disposed at an equal viewing angle relative to the sample surface. For each viewing mode, two sample areas-of-view are provided. The SCE receivers are opposite each other, such that the specular component of each SCE receiver is excluded by the port of the other SCE receiver. The receivers provide the collected light reflected from the sample to a detector which preferably is provided by multiple spectrometers or a single spectrometer having multichannel capability to preferably sense the light from each receiver in parallel.

41 Claims, 7 Drawing Sheets

U.S. PATENT DOCUMENTS

| | | | | |
|---|---|---|---|---|
| 5,098,187 A | * | 3/1992 | Judge | |
| 5,258,363 A | * | 11/1993 | Hed | |
| 5,268,749 A | * | 12/1993 | Weber et al. | |
| 5,272,518 A | * | 12/1993 | Vincent | 356/223 |
| 5,332,908 A | * | 7/1994 | Weidlich | |
| 5,346,049 A | * | 9/1994 | Nakajima et al. | |
| 5,369,481 A | * | 11/1994 | Berg et al. | 356/236 |
| 5,377,000 A | * | 12/1994 | Berends | |
| 5,384,641 A | * | 1/1995 | Imura | |
| 5,408,312 A | * | 4/1995 | Pries et al. | |
| 5,430,540 A | * | 7/1995 | Ohkubo | |
| 5,625,451 A |   | 4/1997 | Schiff et al. | 356/236 |

OTHER PUBLICATIONS

ASTM Standard C523–68 (Reapproved 1981), ASTM Standards on Color and Appearance Measurement, $2^{nd}$ ed. (1987).*

ASTM Standard D2244–85, ASTM Standards on Color and Appearance Measurement, $2^{nd}$ ed. (1987).*

ASTM Standard E179–81, ASTM Standards on Color and Appearance Measurement, $2^{nd}$ ed. (1987).*

ASTM Standard E284–81a. ASTM Standards on Color and Appearance Measurement, $2^{nd}$ ed. (1987).*

ASTM Standard E308–85, ASTM Standards on Color and Appearance Measurement, $2^{nd}$ ed. (1987).*

ASTM Standard E805–81, ASTM Standards on Color and Appearance Measurement, $2^{nd}$ ed. (1987).*

European Search Report of Sep. 23, 1999 (including Annex, EPO Form P0459).

English translation of German Patent DE 44 23 698A 1 (submitted with CPA Application on Oct. 25, 1999).

* cited by examiner

MULTI-CHANNEL INTEGRATING SPHERE

TECHNICAL FIELD

This invention relates generally to integrating spheres and, more particularly, to an integrating sphere with multiple ports for concurrently receiving light directly reflected from a sample under test.

BACKGROUND OF THE INVENTION

The use of integrating spheres for the optical measurement geometry in reflectance colorimetry is a standard practice, and is described in the Commission Internationale De L'Eclairage (CIE) Publication Number 15.2 (Colorimetry), 1986, the disclosure of which is incorporated by reference herein. An integrating sphere is an apparatus with an interior cavity (typically spherical) having a highly reflective, optically diffuse white surface. The simplest integrating sphere design contains two apertures, one which admits light and another which serves as a measurement port where the amount of light on the surface of the sphere can be measured. An integrating sphere has the property that at any point on the inner surface of the sphere the illumination is essentially independent of the direction and location of the incident beam as well as the size of the beam; the inner surface is uniformly illuminated throughout, except at the point of direct illumination. Integrating spheres are used in colorimetry for the precise determination of color for a sample under test.

A common practice in colorimetry is to measure a sample with the specular component of reflection (mirror-like reflection from the surface) either included (SCI mode) or excluded (SCE mode). Other aspects of measurement may include selection of the size of the measured sample surface, spectral content of the illumination, and angle of receiver beam with respect to the sample normal. Instruments designed for colorimetry traditionally measure the sample one configuration at a time (e.g. SCI or SCE mode with a single size of measured area), usually requiring a change of configuration or another instrument to select another mode combination. For example, most integrating-sphere calorimeters are capable of measuring the sample with the specular component either included or excluded. Changing between SCI and SCE modes is usually achieved by the use of a movable segment of the integrating sphere which removes the specular component for SCE measurements or includes the specular component for SCI measurements. In such an instrument, the included/excluded option requires separate measurements with a time between to move the segment and mechanical means to do so.

Many instruments are capable of selecting the size of the area of the sample surface to be measured. Size selection is usually done with a "zoom" optical system or movable lenses/apertures. In such instruments, changing the size of the measurement area requires separate measurements with a time between to move the lens and mechanical means to do so.

Many instruments use a second optical path as a reference measurement to normalize/compensate for changes in the illumination. Such common practice is generally referred to as "dual beam" optics. For the purposes of the discussion herein, such a reference path is not considered a "measurement" path, and is not part of the "multi-channel" principle.

There are some colorimetry instruments with multiple measurement paths currently available. One known example measures the sample SCI and SCE simultaneously with two measurement paths. The instrument is described in U.S. Pat. No. 5,369,481 ("the '481 patent"), the disclosure of which is incorporated by reference herein. The primary path measures the sample in SCI mode at multiple wavelengths. The secondary path measures the sample in SCE mode at one wavelength, and the remaining wavelengths are calculated based on the SCI value at the common wavelength and theoretical knowledge of the wavelength dependence of the specular reflection of the sample. The '481 patent constrains the simultaneous SCE and SCI paths (presumably measuring the same sample area-of-view size) to being "opposite" each other relative to the sample axis normal, and describes only this arrangement of an SCI and SCE port, the number of measurement paths limited to just these two plus the conventional reference path.

Other instruments are equipped with multiple measuring "paths" which measure the color of the sample in one measurement path and measure a different parameter of the sample's appearance, such as gloss, with a second measurement system. An example includes the Color and Appearance Technology, Inc. SPECTRO/plus® Spectrophotometer, the disclosure of the product brochure for which is incorporated by reference herein. The instrument provides a separate measurement system for the gloss; this separate measurement path does not measure the "color" of the sample and has a unique geometry specific to gloss measurement standards, such as ASTM D523, published by the American Society for Testing and Materials (ASTM) of Philadelphia, Pa., the disclosure of which is also incorporated by reference herein. Therefore, the SPECTRO/plus® only has one color measurement path.

There remains a need, therefore, for further improvements in integrating spheres, and particularly, for an integrating sphere which is capable of measuring multiple parameters, such as various specular component modes and/or areas-of-view per specular component mode, without the need for succesive measurements and/or reconfiguration.

SUMMARY OF THE INVENTION

The present invention overcomes the above, and other, limitations of the prior art and the background art by providing an integrating sphere having multiple receivers capable of concurrently receiving optical radiation scattered/reflected from a diffusely illuminated sample surface, with the capability of multiple measurement modes (e.g., multiple SCE, SCE and SCI, multiple SCI), multiple areas-of-view for a given measurement mode, multiple viewing angles per measurement mode, and combinations thereof.

In accordance with an aspect of the present invention, there is provided an integrating sphere, which comprises a housing member having a cavity with an optically diffuse and highly reflective inner surface, the housing member including a sample port where a sample is placed. An optical radiation source provides optical radiation directed toward the inner surface to diffusely illuminate the sample port. A first port is disposed in the housing member and directed toward the sample port along a first line extending at a first angle relative to a first normal to the sample at the intersection of the first line and the sample surface to receive optical radiation scattered from the sample. A second port is disposed in the housing member and directed toward the sample port along a second line extending at a second angle relative to a second normal to the sample at the intersection of the second line and the sample surface to receive optical radiation scattered from the sample concurrently with the reception by the first receiver of optical radiation scattered from the sample surface. Each each of the first and second ports either is (i) an SCI port which receives optical radiation, including a specular component, reflected from the sample port along the corresponding first or second line, or is (ii) an SCE port which receives optical radiation reflected from the sample port exclusive of specular component, the first port and the second port respectively selected from the group consisting of: an SCI port and an SCE port located in non-opposite relationship to each other; a first SCE port and a second SCE port located in opposite relationship to each other; a first SCE port and a second SCE port located in non-opposite relationship to each other; and a first SCI port and a second SCI port located in non-opposite relationship to each other.

In accordance with another aspect of the present invention, the first and second ports are not limited to being either non-opposite each other or opposite each other, and the first and the second port may be respectively selected from the group consisting of: an SCI port and an SCE port located in non-opposite relationship to each other; an SCI port and an SCE port azimuthally displaced by an angle not equal to about pi radians, the SCI port located opposite to said SCE port; an SCI port and an SCE port azimuthally displaced by an angle equal to about pi radians, the SCI port located opposite to said SCE port, said first angle not equal to said second angle; an SCI port and an SCE port azimuthally displaced by an angle equal to about pi radians, the SCI port located opposite to said SCE port, said SCI port and said SCE port viewing respective non-overlapping regions of said sample; a first SCE port and a second SCE port located opposite to said first SCE port; a first SCE port and a second SCE port located in non-opposite relationship to each other; and a first SCI port and a second SCI port located in non-opposite relationship to each other.

In accordance with an aspect of the present invention, multiple measurement paths (i.e., receivers) are used to provide multiple areas of view and specular component included/excluded modes using an integrating sphere-based reflectance colorimeter/spectrophotometer for the measurement of color and appearance. Measurement paths are provided by the fitting of multiple optical receivers to a common integrating sphere, each with its respective viewing port (aperture) in the integrating sphere, and preferably with central axes converging to a common point at the sample (specimen) port of the integrating sphere. Preferably, the measurement paths are at a common angle from the normal to the sample plane (often 8° for colorimetry) at the sample port; the paths can be displaced around the azimuth of the sample-normal axis to separate them, or the receiver paths may be coaxial, or a combination of both. The integrating sphere may be illuminated by a white light source introduced through an additional input port, or, alternatively, the light source may be substantially internal to the integrating sphere. The integrating sphere is used in a conventional way to diffuse the light to provide uniform illumination of the sample. The receiver optics collect the light reflected from the sample at predetermined angles from normal and conduct the light to preferably parallel detection means, such as multiple spectrometers or a single spectrometer having multichannel capability.

BRIEF DESCRIPTION OF THE DRAWINGS

Additional aspects, features, and advantages of the invention will be understood and will become more readily apparent when the invention is considered in the light of the following description made in conjunction with the accompanying drawings, wherein.

DETAILED DESCRIPTION OF THE PREFERRED EMBODIMENT

Figure 1A:
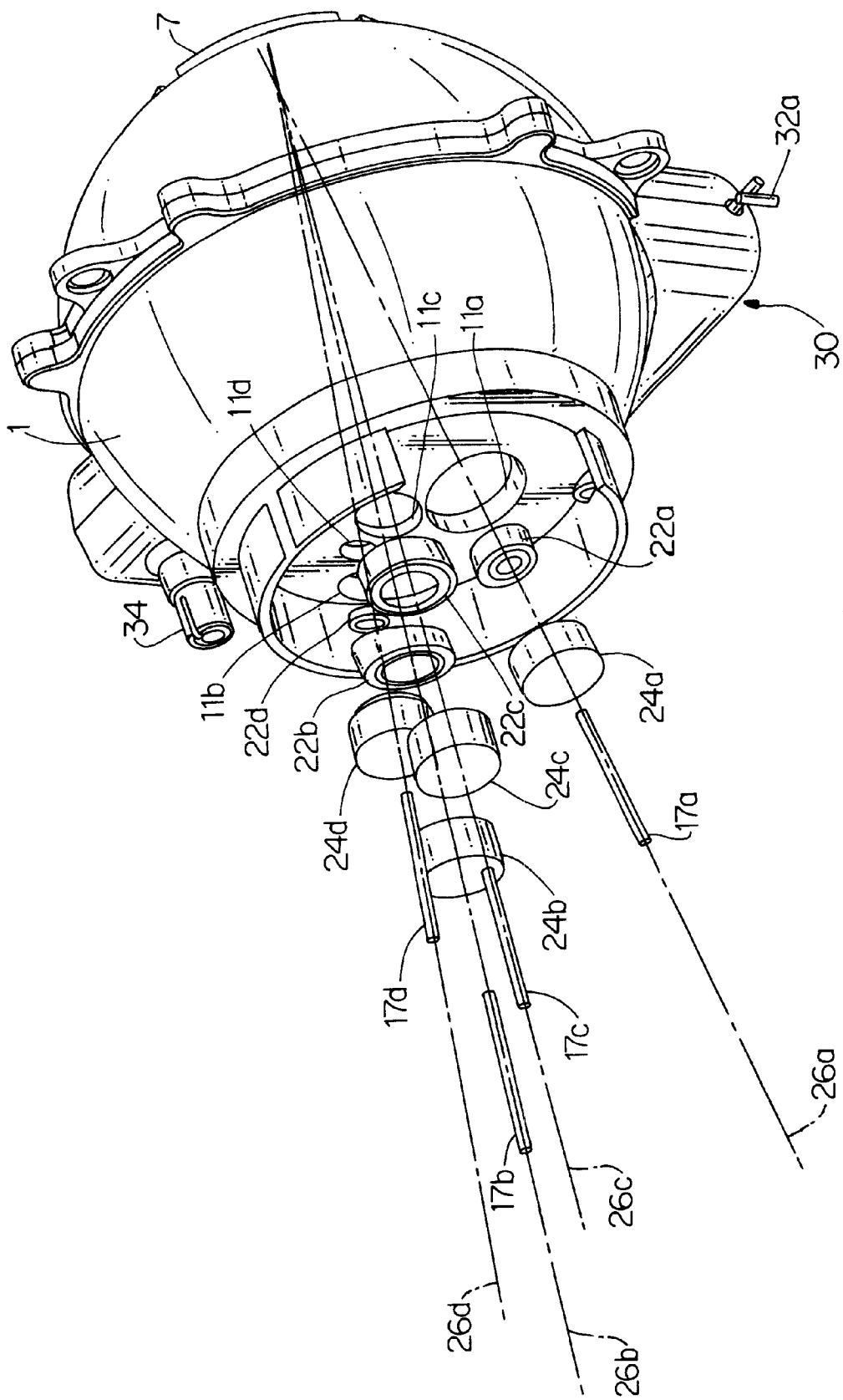
FIG. 1A depicts an isometric view, with certain features of the receivers exposed for clarity, of an integrating sphere according to an embodiment of the present invention.

The present invention provides an integrating sphere which features the capability of multiple measurement modes (e.g., multiple SCE, SCE and SCI, multiple SCI), multiple areas-of-view for a given measurement mode, multiple viewing angles per measurement mode, and combinations thereof, as will be more fully appreciated hereinbelow. It is noted that the term integrating sphere is not intended to limit the interior cavity to a spherical shape, but is used, as understood by one of ordinary skill in the art, to refer to a class of instruments used for measuring light reflectance of a test sample; different shapes of the interior cavity may be implemented.

Prior to describing illustrative embodiments of the invention, certain terminology is introduced for purposes of consistency and clarity of exposition in describing viewing conditions (e.g., spatial/optical location, orientation, and/or relationship of, between, or among port(s), sample, viewing beam(s), etc.) for an integrating sphere which is used in a diffuse reflectance measurement configuration to diffusely illuminate a test sample located at a sample port, and to receive optical radiation reflected from the test sample into receivers associated with viewing ports of the integrating sphere. Conventional colorimeters are often of reverse geometry, that is, with the illumination beam impinging directly on the sample and the detection path receiving light from the wall of the integrating sphere, which integrates the light reflected by the sample. As will be more fully appreciated hereinbelow, the present invention generally is not compatible with such reverse geometry; thus, the terminology used herein applies to the "non-reverse" geometry described hereinabove according to a diffuse reflectance measurement configuration.

As used herein, a port generally refers to a region of the integrating sphere in which the highly reflective, optically diffuse inner surface is absent, and typically includes an aperture formed through the inner wall. A colorimeter integrating sphere includes a sample port and one or more viewing ports, and, as described hereinbelow, may also include a specular exclusion port (SEP) and/or a reference port.

Generally, a viewing port has an associated receiver and is characterized by a viewing beam representing the ray bundle of optical radiation received by the associated receiver directly from optical radiation reflected by the sample. The areal cross section of the viewing beam of a receiver at the associated viewing port may be less than or equal to the overall cross-sectional area of the viewing port itself. Where the port area is greater than the receiver area, the region of the port surrounding the receiver portion typically has low reflectivity.

A ray viewing angle refers to the angle between a ray of the viewing beam and the normal to the sample surface where the ray intersects the sample surface. A viewing beam plane refers to a plane defined by a ray in the viewing beam and the normal to the sample surface at the intersection of the sample surface and the ray. An azimuthal angle between two viewing beams is represented by the angle, in a plane perpendicular to a sample normal, between two viewing planes of the respective viewing beams.

Generally, a viewing beam may include rays which deviate from each other (i.e., are not parallel) within some range (e.g., the incorporated CIE publication prescribes that the angle between the viewing beam axis and any ray of the viewing beam should not exceed 5°), thus resulting in a finite range of azimuthal angles of the viewing rays relative to a given plane, as well as a finite range of viewing angles for the viewing beam. Since, however, a viewing beam is typically symmetric about a viewing axis (i.e., the central axial ray of the viewing beam), this viewing axis is typically used for describing the (effective) viewing angle for the viewing beam as well as the (effective) azimuthal angle relative to the viewing beam.

Also as used herein, generally for SCE mode, a second port is sometimes said to be opposite relative to a first port (also referred to the first port having an opposing port) if a mirror image beam of the first port's viewing beam mirrored from the sample surface (i.e., each ray of the ray bundle specularly reflected by the sample surface) is substantially overlapped by (e.g., encompassed by) the second port such that the specular component of the first port is completely or effectively excluded. Stated alternatively, the second port encompasses substantially the entire region from which optical radiation specularly reflected from the sample surface into the viewing beam of the first port would originate if the second port were not there (i.e., if the region were diffusely scattering). Stated yet another way, the second port is located at the portion of the integrating sphere wall corresponding to substantially all specular (regular) components for the first port.

Accordingly, two ports are said to be opposite each other if the first port is opposite the second port (as described) and the second port is also opposite the first port such that the mirror image beam of the second port's viewing beam mirrored from the sample surface is substantially overlapped by the first port. It is noted that because a port's receiver area may be smaller than the port's area, if two ports are opposite each other, it does not necessarily follow that the viewing beams view overlapping sample surface regions or that the viewing beams have equal viewing angles: the mirror image of each viewing beam may project into the extra-receiver region of the opposing port, and the extra-receiver region of the port(s) may be of sufficient area to allow for differences in viewing angles and/or viewed sample surface regions. For instance, adjacent, non-concentric (e.g., non-overlapping) sample surface regions may be viewed by ports which are opposite to each other and have the same viewing angle; or, a common, overlapping surface region may be viewed by ports which are opposite to each other and have slightly different viewing angles.

It may be understood in accordance with this terminology that a second port may be opposite relative to a first port but the first port may not be opposite to the second port: the viewing beam of the second port mirrored from the sample surface may not be substantially overlapped by the first port, whereas the viewing beam of the first port mirrored from the sample surface may be substantially overlapped by the second port. For instance, the first port and the second port (i.e., their viewing planes) may be azimuthally displaced by about 180° but with unequal viewing angles such that the second port encompasses a region of the integrating sphere inner surface from where the regular component for the first port receiver would originate but the viewing angle of the second port is such that the first port is not located at the region from where the specular component for the first port arrives. Alternatively, the first and second ports may be azimuthally displaced by about 180° with equal viewing angles, but viewing non-concentric (e.g., non-overlapping) sample surface regions, such that the second port encompasses a region of the integrating sphere inner surface from where the regular component for the first port receiver would originate but the viewed sample region displacement is such that the first port is not located at the region from where the specular component for the first port arrives. In another illustrative alternative, two ports may have any respective combination of viewing angles (including equal viewing angles), and may be azimuthally displaced by any angle not equal to about 180° with the first port's projected beam substantially overlapped by the second port, the ports thus viewing non-concentric (e.g., non-overlapping) surface regions of the sample.

It also follows from this terminology that a second port is said to be non-opposite to a first port if the first port's viewing beam mirrored from the sample surface (i.e., the projection of the first port's viewing beam) is not substantially overlapped by the second port, the first port viewing beam having a not insubstantial specular component. In accordance with this general terminology for describing oppositely disposed ports, it also follows that two ports are non-oppositely disposed if neither port is opposite relative to the other port. For instance, the ports (i.e., their viewing planes) may be displaced by an azimuthal angle different from 180° and have any combination of viewing angles provided neither port's viewing beam projection is substantially overlapped by the other port. Alternatively, it may be appreciated that two non-oppositely disposed ports (i.e., their viewing planes) may nevertheless be azimuthally displaced by about 180° if, for example, they have sufficiently different viewing angles and/or they view sufficiently non-concentric (e.g., non-overlapping) sample regions, such that the projection of each beam is not substantially overlapped by the other port.

It is understood that the foregoing description of spatial relationships between ports (and their viewing beams) is a general one which depends on the relative orientations of the viewing beams with respect to the sample plane (e.g., their respective viewing angles and viewing regions, and their relative azimuthal displacement), and which does not depend on a specific integrating sphere geometry or on a predetermined relationship of the viewing beams to each other or to the integrating sphere geometry.

Typically, however, and in accordance with a preferred embodiment of the invention described hereinbelow, each viewing port has a viewing beam that is directed towards the sample along a viewing axis about which the viewing beam is symmetric and which intersects the sample plane at a common point which is typically also the point of intersection of the sample plane by a normal thereto which is a central axis of the integrating sphere (assuming the integrating sphere has a spherical cavity, this central axis passes through the center of the spherical cavity and the center of the sample port). Such symmetry of the viewing beams with respect to a common axis simplifies certain descriptions of relationships between or among ports. For instance, if two ports have equal viewing angles and are azimuthally displaced by about 180°, then they are opposite each other. It is understood, however, that the present invention is not limited to ports having such spatial symmetry with respect to a common axis which is symmetric relative to the integrating sphere cavity. It is also understood that the foregoing terminology is simply a chosen convention for clarity of exposition, and that there are other ways of describing the spatial relationships between or among ports and their viewing beams.

Figure 1B:
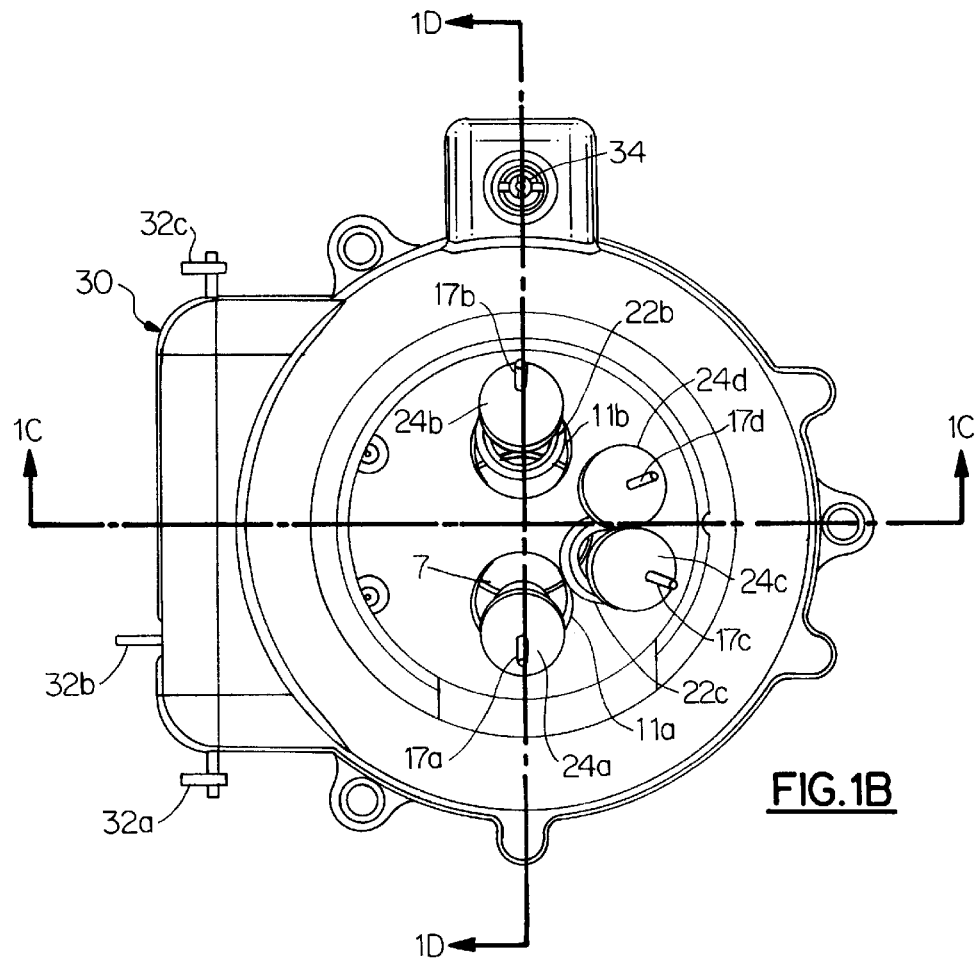
FIG. 1B depicts a plan (top) view, from the receiver side, of the integrating sphere, also with certain features of the receivers spaced away for clarity.
Figure 1E:
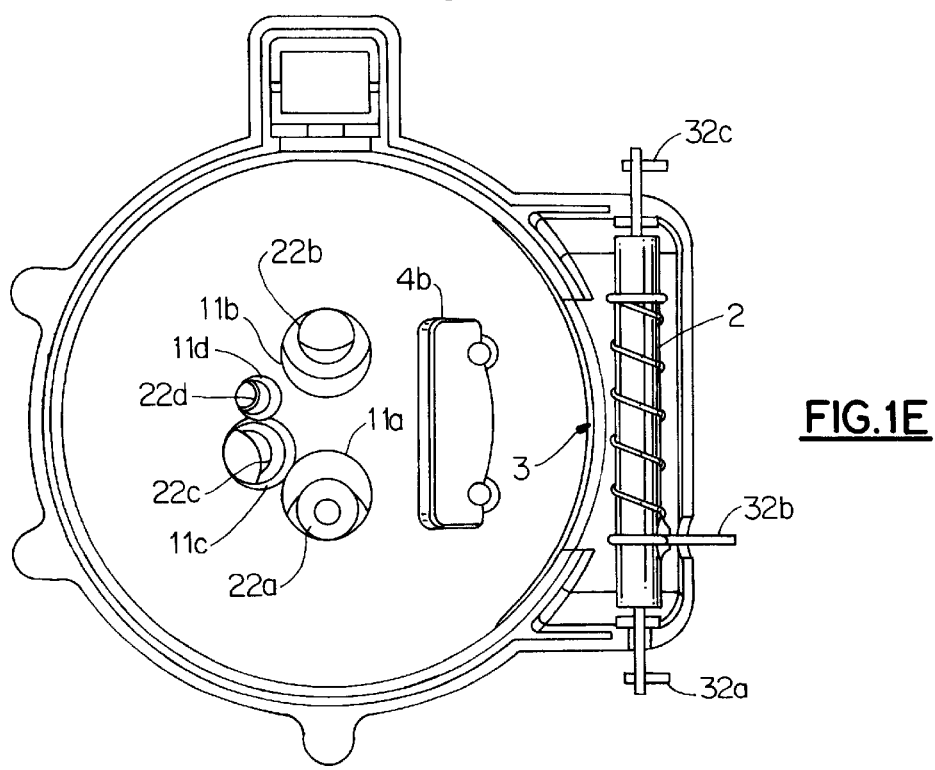
FIG. 1E is a cross-sectional view of the integrating sphere along line IE—IE of FIG. 1D.
Figure 1C:
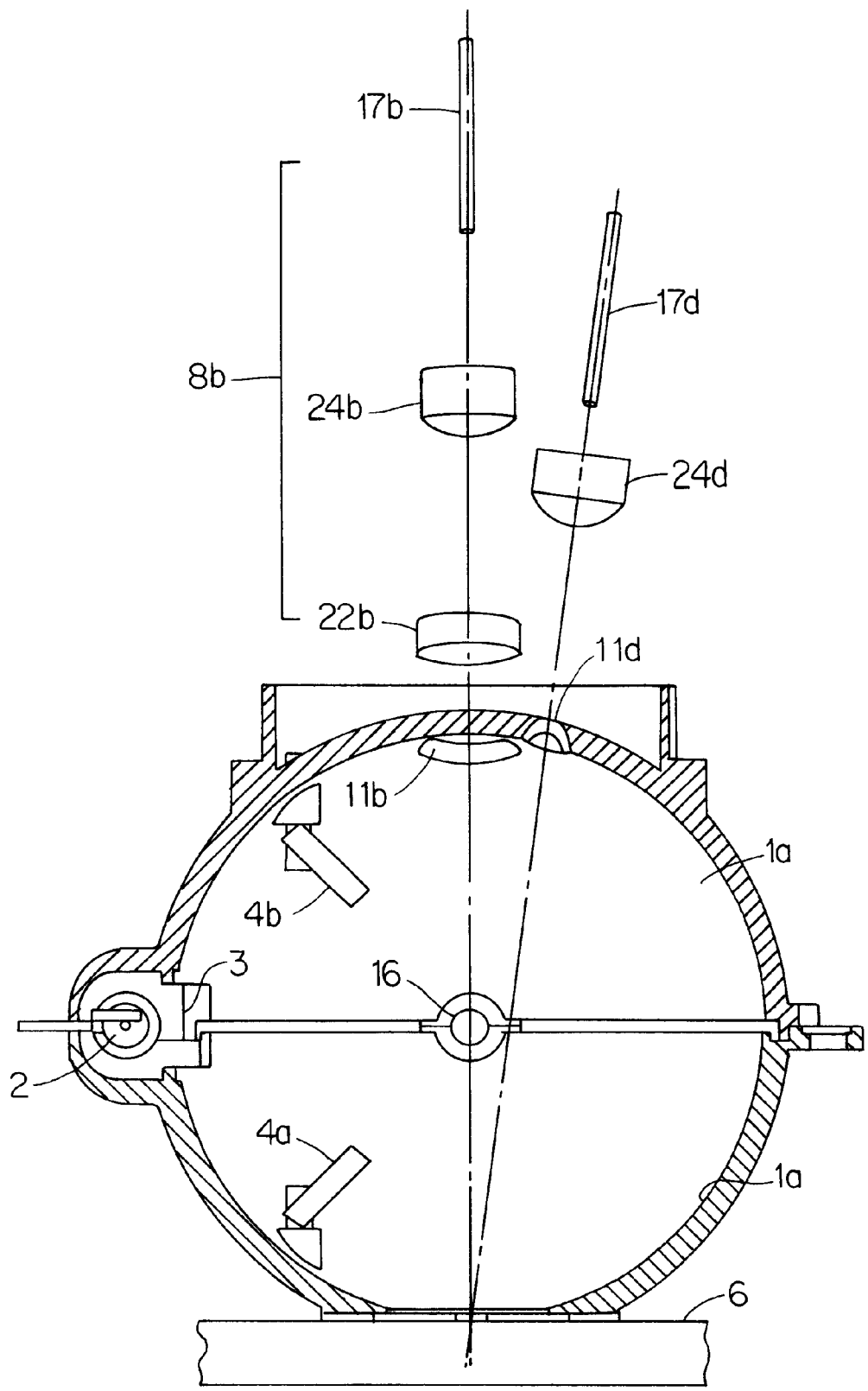
FIG. 1C is a cross-sectional view of the integrating sphere along line IC—IC of FIG. 1B, with certain features of the receivers exposed for clarity.
Figure 1D:
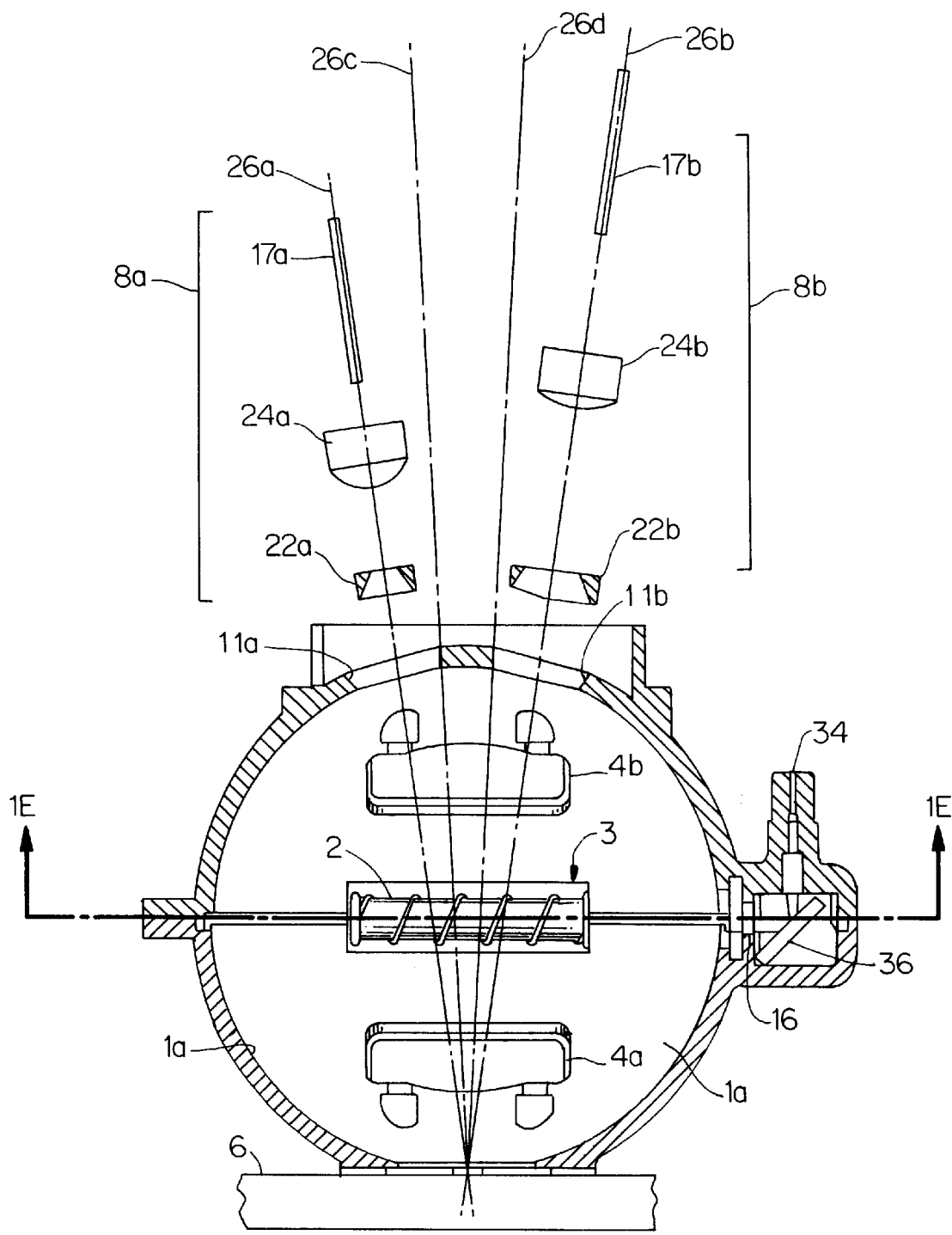
FIG. 1D is a cross-sectional view of the integrating sphere along line ID—ID of FIG. 1B, with certain features of the receivers exposed for clarity.

Referring now to FIGS. 1A–1E there is shown an integrating sphere 1 according to an embodiment of the present invention. More specifically: FIG. 1A depicts an isometric view, with certain features of the receivers exposed for clarity, of an integrating sphere according to an embodiment of the present invention; FIG. 1B depicts a plan (top) view, from the receiver side, of the integrating sphere, also with certain features of the receivers exposed for clarity; FIG. 1C is a cross-sectional view of the integrating sphere along line IC—IC of FIG. 1B; FIG. 1D is a cross-sectional view of the integrating sphere along line ID—ID of FIG. 1B; and FIG. 1E is a cross-sectional view of the integrating sphere along line IE—IE of FIG. 1D.

In more detail, integrating sphere 1 includes two halves to facilitate construction: the two halves may be machined properly to fit one within the other, and appropriately secured with standard fastening mechanisms. Integrating sphere 1 includes a cavity having a highly reflective, optically diffuse surface 1a illuminated with a light source 2 (lamp) which may be coupled to the integrating sphere 1 in a conventional way using an entrance port 3 (aperture in the integrating sphere). Power to the lamp is supplied via lamp leads 32a, 32b, and 32c. By way of example, in an embodiment of the invention, the light source 2 may be a pulsed lamp of high intensity, short duration, and with a full "white" spectrum, such as a pulsed Xenon lamp. The effect is to diffusely illuminate sample 6 at port 7, in a conventional way.

In the present embodiment, lamp 2 is external to the integrating sphere 1 cavity, housed in a lamp cavity 30 adjoined to integrating sphere 1. Lamp 2 may alternatively be placed at least partially internal the cavity of integrating sphere 1, and may be placed substantially internal to the integrating sphere cavity to achieve the following advantages: optical flux efficiency, mechanical simplicity, small size, and reduction of port apertures which allows a smaller integrating sphere 1 to be used for a given sample port 7 size while conforming to standards for integrating sphere design. Also, in accordance with conventional practice, the lamp may be external to the sphere and projection optics (e.g., lens, etc.) may be used to relay or project flux from the lamp through the entrance port and to a spot at the far side of the integrating sphere interior.

A baffle 4a with highly reflective, optically diffuse surface is used in a conventional way to block light rays from directly illuminating the sample 6 (shown in FIGS. 1C and 1D, only) from the lamp, or from the entrance port 3 if used. Similarly, baffle 4b prevents light rays originating at entrance port 3 or lamp 2 from directly illuminating portions of the sphere surface from where specular flux for the SCI receivers originates.

As shown, diffusely illuminated sample 6 is viewed by multiple optical receivers 8a–d (i.e., four receivers in the present embodiment), each of which receives a portion of optical radiation reflected from sample 6 and provides it to a sensor or detector used to analyze the spectral content of the received optical radiation. More particularly, shown are multiple viewing ports including specular-component-excluded (SCE) port 11a, SCE port 11b, specular-component-included (SCI) port 11c, and SCI port 11d. Each port has an associated receiver comprising associated receiver optics (shown exposed) according to the present embodiment: SCE port 11a has a receiver 8a including aperture stop 22a, lens 24a, and fiber 17a; SCE port 11b has receiver 8b including aperture stop 22b, lens 24b, and fiber 17b; SCI port 11c has receiver 8c including aperture stop 22c, lens 24c, and fiber 17c; SCI port 11d has a receiver 8d including aperture stop 22d, lens 24d, and fiber 17d. Each receiver 8a–d is directed at sample port 7 along a corresponding one of viewing axes 26a, 26b, 26c, and 26d, which according to the present embodiment, converge to a common point of intersection at the surface of sample 6. It is understood that actual components of the receivers may differ, depending on design criteria, applications, preference, etc.

The optical receivers 8a–d of the present embodiment are located at a same predetermined viewing angle from the sample normal (less than 10° to comply with standards for colorimetry, 8° in the present embodiment) and each has its own associated receiver viewing port 11a–d in the integrating sphere 1. For each viewing mode (i.e., SCE and SCI), the receivers have two subtense angles, corresponding to two sample area sizes. The optical receivers 8a–d and their respective receiver viewing ports 11a–d are displaced azimuthally, thereby advantageously maintaining the same predetermined viewing angle from the sample normal, and the azimuthal displacements are chosen to conveniently fit optical receivers 8a–d (and their associated viewing ports 11a–d), each designed with a combination of chosen parameters. The parameters include, but are not limited to, the measured size of the sample surface, the subtense angles of the receivers, and the inclusion (SCI) or exclusion (SCE) of the specular-reflected light. Additional and non-exclusive parameters (not used in the present embodiment) include multiple viewing angles, and different viewing regions of the sample surface (e.g., non-overlapping, non-concentric).

Integrating sphere 1 includes one SCE mode receiver and one SCI mode receiver for each of two different measured areas-of-view (four receivers total). The two SCE receivers 8a and 8b, having viewing axes 26a and 26b which intersect the sample at a common point, have equal viewing angles and are azimuthally displaced by 180°, and are thereby opposite each other. Further, SCE ports 11a and 11b are sized appropriately to exclude substantially all specular rays for the respectively opposing associated SCE receivers 8b and 8a. SCI receivers 8c and 8d are placed out of the plane defined by the viewing beams of SCE receivers 8a and 8b, and also at the same predetermined viewing angle from the common sample normal located at the intersection of the sample by the viewing axes, such that the specular component is provided by the inclusion of the integrating sphere surface (no ports) at the regions intersected by the respectively projected SCI receiver viewing beams.

As described, in the embodiment of the invention illustrated in FIGS. 1A–1E, each SCE port is designed to exclude substantially all specular components for the opposing SCE receiver. Such a shared arrangement of SCE/viewing ports advantageously reduces the total port area required to implement a plurality of SCE ports. It may be appreciated, however, that alternative embodiments of the invention may include a separate aperture (port) which does not have an associated receiver and which is appropriately sized and located opposite to an SCE receiver to exclude the specular component origin of the reflected light. Such an aperture is common practice which is known as a specular exclusion port (SEP, also referred to as a light trap), and generally refers to a portion of the integrating sphere's inner surface which does not reflect light, but substantially absorbs it, and which is opposite to an SCE port receiver.

As with frequent conventional practice, integrating sphere 1 preferably includes an added receiver, having associated reference port 16, which provides a measurement of the illumination which is not a direct reflection from sample 6 and preferably not directly incident from lamp 2 or lamp port 3. The viewing beam received via reference port 16 is referred to as a reference beam, and can be used to correct or to control the lamp 2 fluctuations and to compensate for the influence of the sample 6 reflectance on the integrating sphere 1 illumination. In FIGS. 1A–1D, reference port 16 location and its associated receiver characteristics (e.g., viewing axis orientation, subtense angle) are such that only light diffusely reflected from optically diffuse surface 1a of integrating sphere 1 is received. As shown, in order to facilitate common orientation of optical fibers for the present embodiment, the reference beam is conveniently redirected by fold mirror 36 into an optical fiber (not shown) coupled to reference fiber mount 34. It is appreciated that for the current invention, this reference path is not considered or counted as one of the multiple measurement paths.

The spectral content of the optical radiation collected (received) by each of the multiple receivers is analyzed by any of a variety of conventional means, such as filters or spectroscopic optics and appropriate signal processing (not illustrated). Preferably, the optical radiation collected (received) concurrently (in parallel) by the multiple optical receivers 8a–d is detected (i.e., converted from an optical to an electrical signal) in parallel for each receiver, and further, is also detected in parallel spectrum-wise (i.e., for each receiver, the complete spectrum is detected in parallel). In addition, as more fully described hereinbelow, the optical radiation received by the multiple optical receivers 8a–d is detected substantially simultaneously. Analysis of the detected signals may be performed, for example, in order to condition the detected signal and calculate the sample's color using standard formulae, as in the incorporated CIE reference. For clarity, it is noted that, as used herein, receiving optical radiation is distinguished from detecting optical radiation: the former is used to refer to optical radiation scattered/reflected from the sample surface being coupled into (accepted by) a receiver, whereas the latter is used to refer to received optical radiation being sensed (e.g., converted to an electrical signal) by a detector. Moreover, as used herein, receivers (or ports) are said to concurrently receive optical radiation when optical radiation scattered/reflected from the sample impinges on the receivers in parallel; this concurrent reception does not mean that the concurrently received optical radiation is necessarily also detected concurrently or in parallel, although, as described hereinabove and more fully hereinbelow, such concurrent or parallel detection is generally preferable.

In a preferred embodiment of the present invention, such parallel detection is implemented by a single spectrometer with a two dimensional detector array and a segmented entrance slit and a single diffraction grating, as described by Palumbo et al. in commonly assigned U.S. application Ser. No. 09/041,233, entitled "Concentric Spectrometer", filed Mar. 12, 1998, and which is incorporated by reference herein. Each segment of the slit is illuminated by a corresponding receiver path, which may be accomplished with fiber optic light guides 17a–17d. Thus, the multiple optical receivers 8a–8d can be conveniently and advantageously detected simultaneously using a single common spectrometer. Additionally, the reference beam may also be advantageously detected and processed in parallel by such a multi-channel spectrometer. It may be appreciated, however, that alternative apparatuses and/or methods may be implemented for concurrently, but not necessarily precisely simultaneously, detecting the optical signals received in parallel by the different SCI/SCE receivers. For instance, signal detection may be time multiplexed among the channels. Alternatively, even where parallel detectors are used, the channels need not be synchronously sampled; e.g., each channel may be independently gated and/or have a different sampling rate and/or sampling time.

Figure 2A:
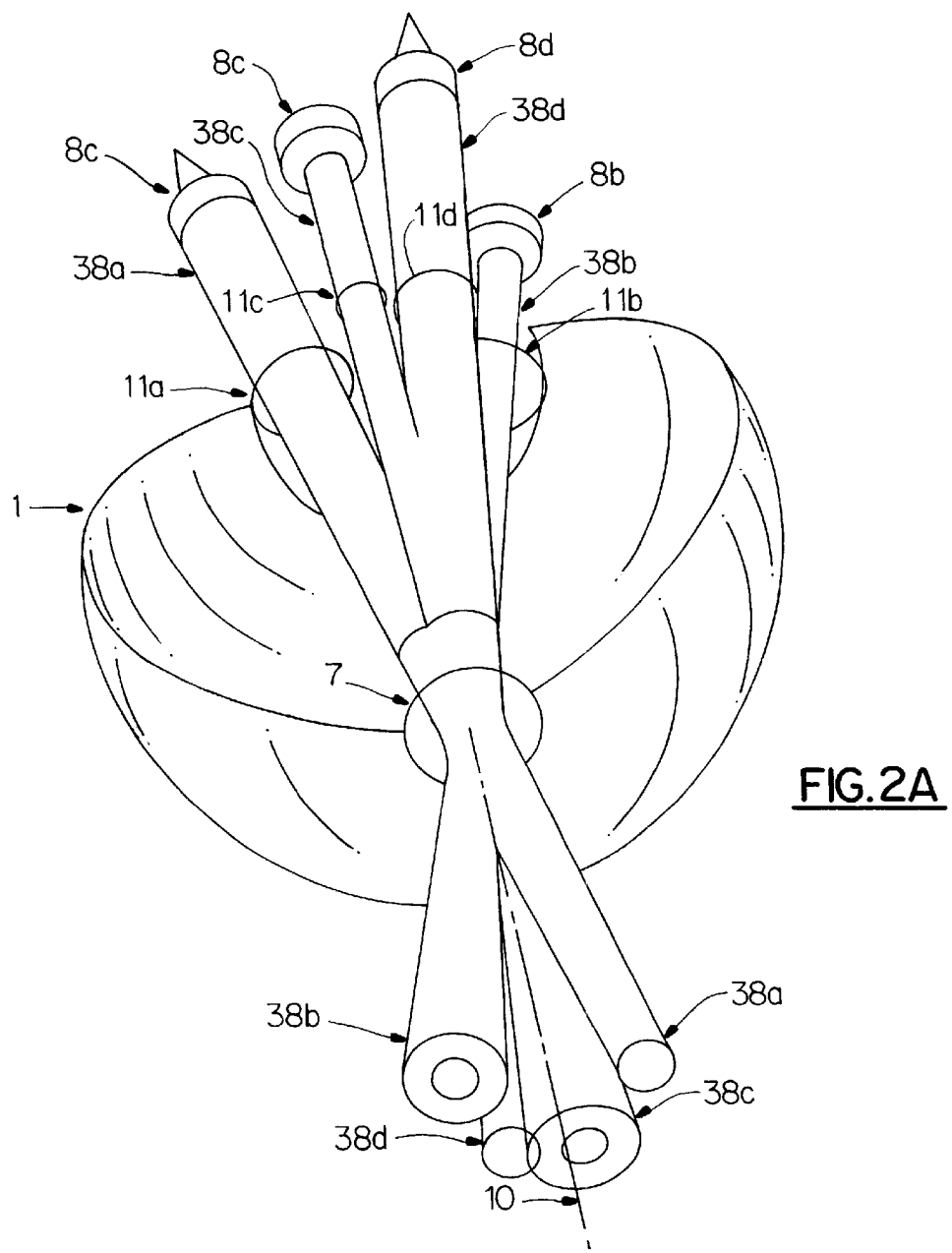
FIG. 2A illustrates a schematic cut-away view of the integrating sphere of FIGS. 1A–1E, with schematic depictions of ray bundles for the receivers and associated ports, so that the relationship among the viewing beams of a preferred embodiment may be visualized.
Figure 2B:
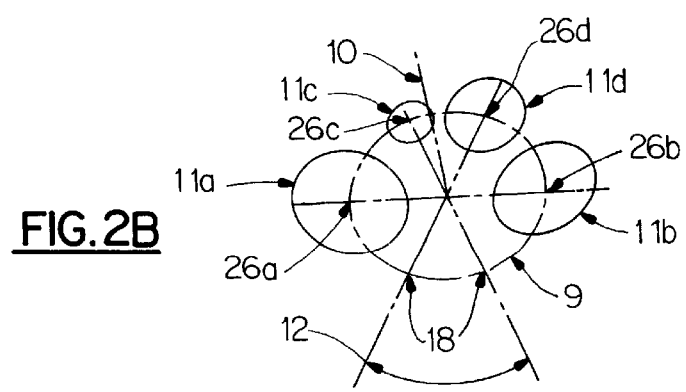
FIG. 2B shows a projection onto a plane parallel to the sample surface of the receiver viewing ports and viewing axes, as depicted in FIG. 2A, so that the mutual relationships of the ports and viewing axes at the rear (i.e., top portion away from the sample port) of the integrating sphere of FIGS. 1A–1E may be more easily visualized.

Referring now to FIG. 2A, there is illustrated a cut-away view of schematic integrating sphere 1 with schematic depictions of ray bundles 38a–38d for corresponding receivers 8a–8d and associated ports 11a–11d, so that the relationship among the viewing beams of a preferred embodiment may be visualized. Also, referring to FIG. 2B, placed in relation to FIG. 2A, there is shown a projection onto a plane parallel to the sample surface of receiver view ports 11a–11d, viewing axes 26c and 26d (and their projections) of SCI ports 11c and 11d, and viewing axes 26a and 26b of SCE ports 11a and 11b, so that the mutual relationships of the ports and viewing axes at the rear (i.e., top portion away from sample port 7) of the integrating sphere may be more easily visualized. It is noted that in FIGS. 2A and 2B, the schematic depiction of ray bundles preserves the general spatial orientation, but does not preserve the relative sizes, of viewing beams and ports shown in FIGS. 1A–1E. Also identified for reference in FIG. 2B are: an example of an azimuthal displacement angle 12 between SCI ports 11c and 11d (i.e., angle between the viewing planes); common sample normal 10 located at the intersection of the sample by the viewing axes 26a–d; circle 9 defined by the projection of the points of intersection of the viewing axes at the same viewing angle and their corresponding viewing ports; and central points 18 of origination of specular inclusion viewing beams at the rear (i.e., internal surface away from the sample port) of the integrating sphere 1, as would be reflected from the specular reflecting surface of the sample 6. FIGS. 2A and 2B together show the relationship between the ports and the specular components of the beams after reflecting off the sample.

Accordingly, it is appreciated that in accordance with the present invention, FIGS. 1A–1E illustrate an embodiment of an integrating sphere having multiple viewing ports, with all of the viewing ports have equal viewing angles, the two SCI ports having different sample areas of view, and the two SCE ports also have two different sample areas of view. Advantageously, the SCE ports are disposed opposite each other such that each excludes the specular components for the receiver of the other, thus reducing the overall port area of the integrating sphere.

It is appreciated that various alternative implementations of the present invention are possible based, as described above, on selection of various parameters including specular component types (i.e., SCI mode and/or SCE mode), number of ports, viewing angles, azimuthal displacements, area-of-view for each port, subtense angles, and viewed sample region for each port. Development of a given design may be dependent not only on certain physical constraints or guidelines, but also on the application or market. For instance, in some applications it is desireable to have a large area-of-view to measure a substantial portion of the sample that provides an average color of a surface that has some variation using a single measurement. It may alternatively or additionally be desireable to have a very small area-of-view to measure a sample that is of small dimension, or a small portion of a multi-colored surface such as a printed pattern or a color bar on a proof sheet, or even to measure the small scale variations of a larger colored surface. Having substantially different, large and small, area-of-views in the same colorimeter may also be generally desireable in order to provide a single integrating sphere having utility for many applications (i.e., multipurpose) or for detecting variations in a sample.

It is understood that the maximum number and size of ports is limited by the sphere diameter which, in order to comply with existing standards, cannot have a total port area (sum of all apertures) that exceeds a certain percentage (3 to 5%, depending on the standards of choice) of the total internal surface area of the sphere. As also is known, the sample port must be slightly larger than the overall region viewed by the receivers to allow for sample translucency (according to existing standards) and to allow for alignment tolerances.

The azimuth angles typically are chosen to adequately separate the viewing ports from one another and from portions of the sphere comprising the origins of specular light for the SCI receivers. These origins of specular light are areas of the sphere surface that are opposite their respective SCI receiver apertures as mirrored from the sample surface, and are of a size that includes preferably all rays that the receiver optics collect by such specular reflection from the sample surface. No ports should intrude those portions of the sphere surface so described. Light traps (SEP ports) or other SCE ports used to remove the specular origin for SCE receivers must be of sufficient size to exclude preferably all rays that the receiver optics would collect by specular reflection from the sample surface.

The size of the receiver ports, specular exclusion ports and specular inclusion origins required are dependent on several parameters of each respective receiver design, including: the sample area-of-view size, the receiver subtense angle, the aperture and focal conjugate positions of a beam forming optic if used (such as a lens), aberration characteristics of the beam forming optic, margin for each beam to ports (respective receiver aperture and specular exclusion) as prescribed by existing standards and/or alignment tolerances, size of the integrating sphere, etc.

As described for the hereinabove embodiment, there is an advantage in opposing SCE ports such that they each effectively act as a specular exclusion port for the receiver of the other SCE port. Such an arrangement reduces the number of ports required for a given number of receivers, and allows more receivers of given parameters to be used in a sphere of the same size.

In the hereinabove embodiment, the receivers' axes are at a same predetermined angle from the sample normal axis, and converge to a common point on the sample surface, the point forming the center of the sample port aperture. For certain applications, however, there may be utility in having receivers at different angles from the sample normal axis and/or not converging to a common point on the sample.

It may be appreciated, therefore, that there are many possible variations for implementing an integrating sphere in accordance with the present invention. In more detail, for example, although SCE ports 11a and 11b are shown opposite each other, as described, alternatively they may be positioned non-opposite each other (i.e., such that neither port is opposite the receiver of the other port), with each SCE port's receiver having an opposing SEP to exclude the specular component (e.g., (i) SCE ports azimuthally displaced by about 180° but with unequal viewing angles, or (ii) SCE ports azimuthally displaced by an angle not equal to about 180° and having any respective combination of viewing angles, including equal viewing angles).

Alternatively, the illustrative integrating sphere of FIGS. 1A–1E may include two additional SCE ports which are opposite to each other (or a single additional SCE port with opposing trap). For example, relative to opposing SCE ports 11a and 11b, the additional opposing SCE ports (or additional SCE port and opposing trap), may be: (i) azimuthally displaced by about 0° (or, equivalently, by 180°) but at different viewing angles, each one of the additional SCE ports having any general viewing angle and/or area-of view, or (ii) displaced azimuthally by an angle not equal to about 0° (or equivalently, 180°) and having any viewing angles, including viewing angles equal to each other and to those of SCE ports 11a and 11b.

Additionally, it may be appreciated that there are myriad implementations possible with respect to orientation and arrangement of SCI ports. For instance, SCI ports 11c and 11d alternatively may be displaced by different azimuthal angles (e.g., 90°) and/or disposed at different viewing angles from each other and/or modified to have the same viewing area. Further, one or more additional SCI ports may be added at any appropriate locations on the integrating sphere.

In these arrangements of two or more SCE ports and/or two or more SCI ports, providing azimuthal displacement (e.g., of about 90°) between or among SCE ports and/or between or among SCI ports may be useful for measuring and/or accounting for various appearance or surface characteristics (e.g., striations, texture, etc.) of the sample (e.g., fabric, weaves, embossings, etc.) which may give rise to azimuthally anisotropic reflectance.

Figure 3A:
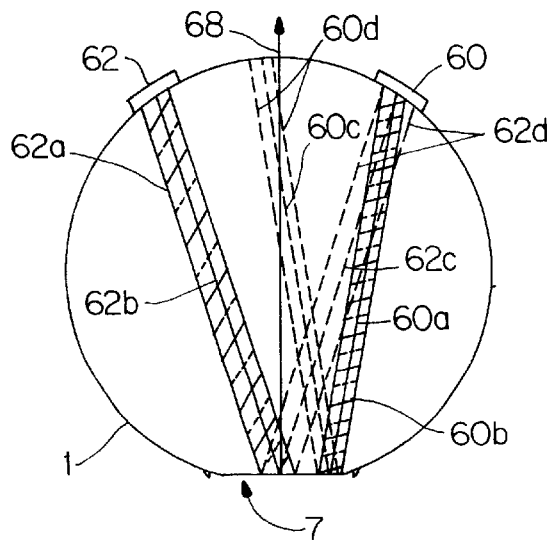
FIG. 3A and FIG. 3B show simplified schematic cross-sectional and top views, respectively, of an integrating sphere having an SCI port opposing the receiver (viewing beam) of an SCE port which does not oppose the receiver (viewing beam) of the SCI port, in accordance with an illustrative embodiment of the present invention.
Figure 3B:
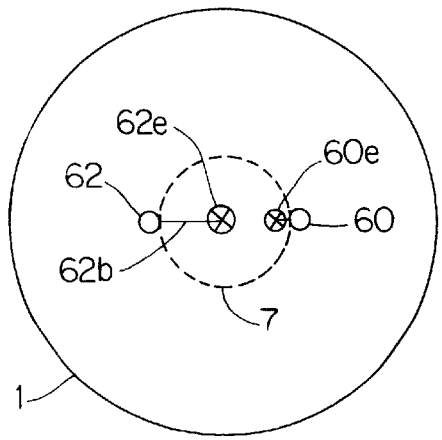

As an additional example of variations within the purview of the present invention, although the embodiment and illustrative variations described hereinabove includes all viewing beam axes converging to a common point at the sample, alternative embodiments may be implemented wherein viewing axes of different viewing beams do not all converge onto a common point. For instance, viewing axes may intersect the sample at different locations and the corresponding viewing beams may view overlapping sample regions (e.g., a larger viewing area of a first viewing beam encompassing a smaller viewing area of a second viewing beam, or may view two viewing areas each viewing both a common and a separate viewing region) or non-overlapping sample regions. Each sample region may be viewed by more than one viewing beam. For purposes of clarity of exposition, consider the following illustrative port configurations having non-overlapping sample viewing areas:

(1) An SCI port opposing the receiver (viewing beam) of an SCE port which does not oppose the receiver (viewing beam) of the SCI port. As a first example, referring to FIGS. 3A and 3B which show simplified schematic cross-sectional and top views, respectively, of an integrating sphere 1 with sample port 7 and central axis 68, SCI port 60 and SCE port 62 (i.e., their viewing planes) may be azimuthally displaced by about 180° but with unequal viewing angles (i.e., the respective angles between each one of viewing axes 60b and 62b and each corresponding sample normal where the respective viewing axis intersects the sample) such that SCI port 60 encompasses a region of the integrating sphere inner surface from where the regular component for the the viewing beam 62a of the receiver of SCE port 62 would originate but SCE port 62 is not located at the region of the integrating sphere surface from which the specular component for the viewing beam 60a of the receiver of SCI port 60 originates. More specifically, as schematically shown by SCI specular viewing axis 60c (which is the specular reflection of SCI viewing axis 60b) and SCI bounding specular rays 60d (which are the specular reflection of the outer rays of viewing beam 60a), the origin of the specular component for SCI port 60 is located on a diffusely and highly reflective inner surface of integrating sphere 1. Conversely, as schematically depicted by SCE specular viewing axis 62c (which is the specular reflection of SCE viewing axis 62b) and SCE bounding specular rays 62d (which are the specular reflection of the outer rays of viewing beam 62a), SCI port 60 encompasses the region from where the specular component for SCE port 62 would originate. In this example, SCI port 60 and SCE port 62 are shown as viewing non-overlapping areas of view 60e and 62e, respectively, of the sample surface.

Figure 4A:
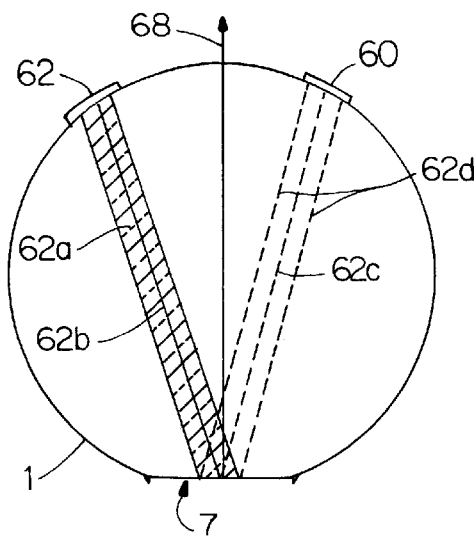
FIG. 4A and FIG. 4B show simplified schematic cross-sectional and top views, respectively, of an integrating sphere having an SCI port opposing the receiver (viewing beam) of an SCE port which does not oppose the receiver (viewing beam) of the SCI port, in accordance with another illustrative embodiment of the present invention.
Figure 4B:
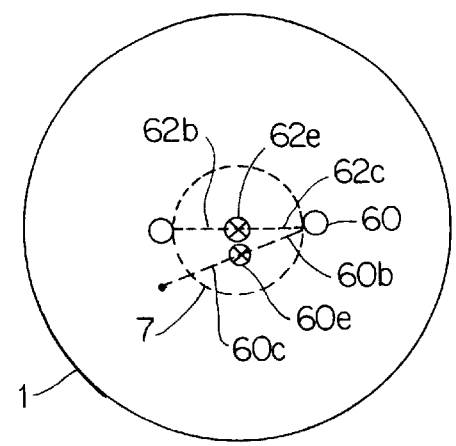

Alternatively, as a second example, referring to FIGS. 4A and 4B SCI port 60 and SCE port 62 (their viewing planes) may be azimuthally displaced by any angle not equal to about 180°, with SCI port 60 and SCE port 62 having any respective combination of viewing angles (within the limits of the integrating sphere geometry), including equal viewing angles, with the projection of the SCE viewing beam reflected from the sample surface impinging on the SCI port. More specifically, as for the previous example, as schematically shown by SCI specular viewing axis 60c (which is the specular reflection of SCI viewing axis 60b), the origin of the specular component for SCI port 60 is located on a diffusely and highly reflective inner surface of integrating sphere 1. Conversely, as schematically depicted by SCE specular viewing axis 62c (which is the specular reflection of SCE viewing axis 62b) and SCE bounding specular rays 62d (which are the specular reflection of the outer rays of viewing beam 62a, SCI port 60 encompasses the region from where the specular component for SCE port 62 would originate. In this example, SCI port 60 and SCE port 62 are also shown as viewing non-overlapping areas of view 60e and 62e, respectively, of the sample surface.

(2) A second SCE port opposing the receiver (viewing beam) of a first SCE port which does not oppose the receiver (viewing beam) of the second SCE port. The second SCE port may be opposed by a SEP or a third SCE port or a SCI port. Various viewing angle and azimuthal angle configurations for the first and second SCE ports are possible, directly analogous to the SCI port and SCE port of the latter example.

(3) A shared viewing port having multiple non-coaxial receivers.

As yet a further example of variations within the purview of the present invention, the integrating sphere may include coaxial receiver paths (i.e., a single port with a plurality of receivers). More particularly, coaxial receivers can be provided to increase the number of available receivers. An implementation may employ coaxial lenses of different focal lengths and correspondingly different diameters, as would be desired to provide different areas-of-view, and placing them one in front of the other, smaller diameters closer to the sample. The larger lens(es) would peer around the smaller, the latter forming a central obscuration to the larger. The central obscuration can often be tolerated simply as a loss in available sample light for the larger lens(es). The focus of the smaller lens(es) can be transmitted to the analysis means by providing a fold mirror or a fiber optic guide or similar, so as to minimize interference with the larger receiver(s). Of course, curved mirrors may be used instead of the lenses. Another implementation for providing coaxial receivers employs zone plates: a zone plate with a Fresnel pattern is known to have multiple focal lengths, for which a receiver can be used at or near two or more foci, using the transmitting/folding techniques already described. Yet another implementation for providing coaxial receivers is by combining their axes using beamsplitter(s) as beam combiners. The coaxial receivers may be implemented as all SCI receivers, all SCE receivers, or a combination of SCI and SCE receivers. The specular component for SCE receiver(s) implemented coaxially with SCI and/or SCE receiver(s) may be blocked by another SCE port (coaxial or individual) or by a SEP. Implementing coaxial SCE ports coaxially with the sample normal provides a plurality of SCE ports without the need for any additional port to block the specular components.

Figure 5:
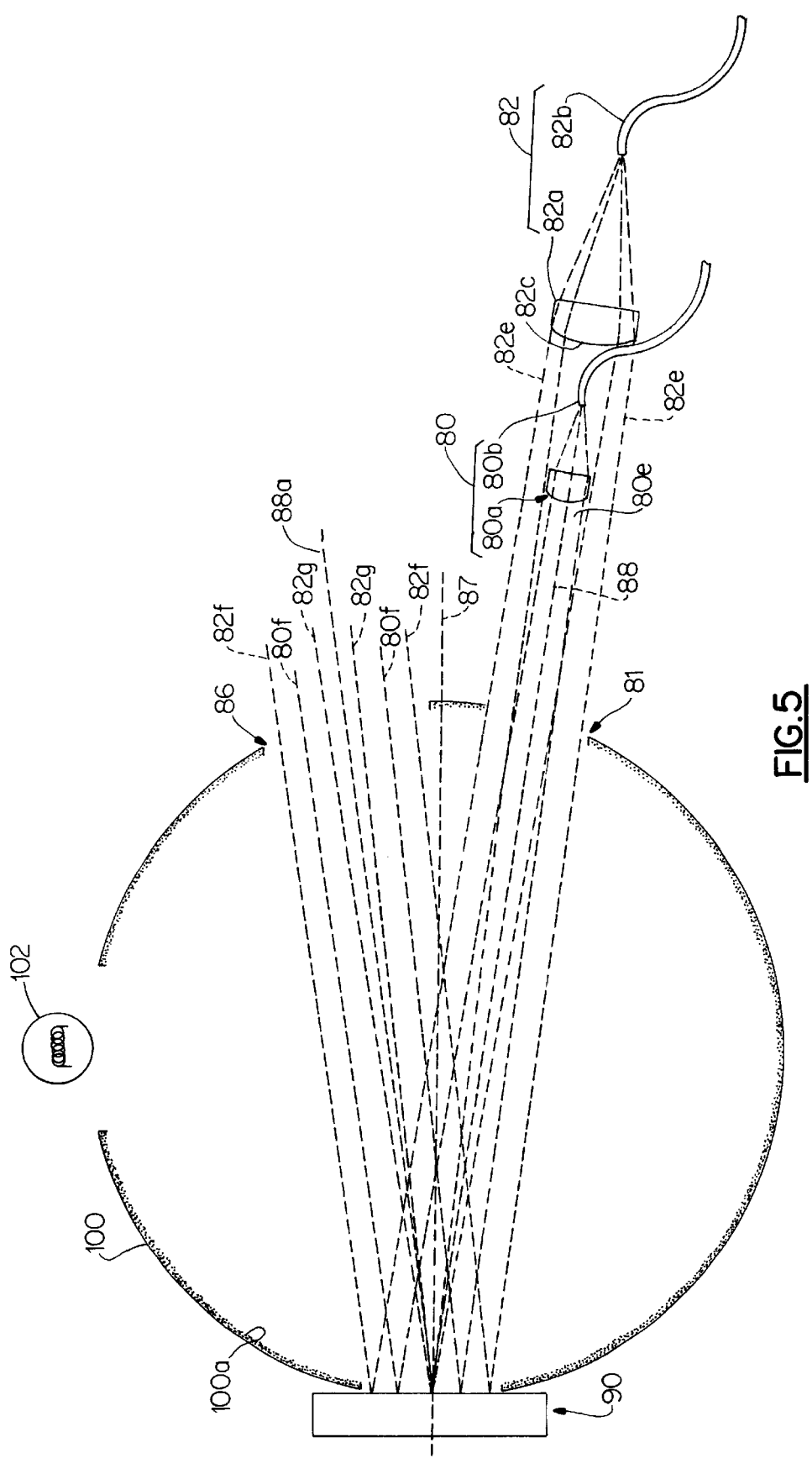
FIG. 5 schematically shows an implementation of an integrating sphere including coaxial receivers according to an illustrative embodiment of the present invention. In this illustrative embodiment

By way of example, FIG. 5 schematically shows an implementation of a coaxial receiver according to an illustrative embodiment of the present invention. In this illustrative embodiment, coaxial small area receiver 80 and large area receiver 82 sharing viewing port 81 are both SCE receivers, and are shown as opposed by an SEP 86 which is schematically shown as an absence of a portion of integrating sphere 100 and its inner diffuse, highly reflective surface 100a. Small area SCE receiver 80 and large area SCE receiver 82 have a common receiver axis 88 along which the receivers are directed toward sample 90 which is diffusely illuminated by optical radiation indirectly incident from lamp 102 via integrating sphere 100. Small area receiver 80 includes lens 80a optically coupled to optical fiber 80b, whereas large area receiver 82 includes lens 82a optically coupled to optical fiber 82b. Lens 82a includes a central obscuration area 82c to prevent receiving optical radiation from the small area receiver, thus ensuring that large area receiver 82 only receives optical radiation directly from sample 90. Also shown for reference and clarity of exposition are schematic depictions of: sample normal 87; specular receiver axis 88a corresponding to the specular reflection of receiver axis 88; small area viewing beam 80e; large area viewing beam 82e; bounding small area specular rays 80f which correspond to the outer boundaries of the specular rays for small area viewing beam 80e; outer large area specular rays 82f which correspond to the specular rays for the outer boundaries of large area viewing beam 82e; and inner large area specular rays 82g which correspond to the specular rays for the inner boundaries of large area viewing beam 82e. From these reference lines, it can be seen that in this implementation small area receiver 80 and large area receiver 82 view concentric areas of sample 90. It is understood that coaxial SCE receivers may alternatively be opposed by another sample viewing port, such as an SCE port (e.g., itself having one or more SCE receivers). It is also understood that, more generally, an integrating sphere in accordance with the present invention may include one or more ports each having coaxial receiver arrangements, and that additional ports having single receivers may also be included in combination with one or more ports having coaxial receivers.

These foregoing variations with respect to SCE and SCI port arrangements are merely illustrative of the many possible variations according to the present invention with respect to azimuthal displacement, area-of-view, viewing angle, and location-of-view (i.e., location of area-of-view as may be defined by the sample intersection by the viewing axis) of an integrating sphere having two or more SCI ports, or at least one SCI port and at least one SCE port, or two or more SCE ports. It is understood that, as described above, selection of a particular configuration may depend on various factors, such as intended application(s) (e.g., colorimetry, gloss, texture, etc.) and measurement standards.

As may be appreciated from the foregoing description, and as may be farther appreciated by practicing the present invention, an integrating sphere according to the present invention includes myriad features, advantages, and attendant advantages. For instance, advantages of receiving a plurality of viewing beams in parallel include: multiple data sets may be provided by a single measurement step, no moving parts or time delay required to change modes (e.g., SCE, SCI, different areas of view for SCE and/or SCI), electrical power is efficiently used (e.g., reduced time needed to power lamp compared to multiple measurements, no parts need be electromechanically moved), component sizes may be small, and overall structure will be durable (e.g., from no moving parts). The presence of both SCI and SCE modes for a given area-of-view can quickly and conveniently provide an estimate of the gloss of the sample surface. The presence of multiple areas-of-view provides capability for quickly measuring or estimating sample uniformity and/or sample translucency. Additionally, various azimuthal angles between SCE and/or SCI provide the ability to extract other appearance parameters (in addition to the color) from the data sets acquired, such as surface flatness or texture. Having a simultaneous reference measurement also provides optimum correction. These features and advantages provide substantial benefits particularly well suited for portable instruments, as well as for convenient non-portable applications.

Although the above description of illustrative embodiments of the invention, and various modifications thereof, provides many specificities, these enabling details should not be construed as limiting the scope of the invention, and it will be readily understood by those persons skilled in the art that the present invention is susceptible to many modifications, adaptations, and equivalent implementations without departing from this scope and without diminishing its attendant advantages. It is therefore intended that the present invention is not limited to the disclosed embodiments but should be deemed in accordance with the claims which follow.

What is claimed is:

1. An integrating sphere, comprising:
   a housing member having a cavity with an optically diffuse and highly reflective inner surface;
   said housing member including a sample port where a sample is placed;
   an optical radiation source which provides optical radiation directed toward said inner surface to diffusely illuminate said sample port;
   a first port disposed in said housing member and directed toward said sample port along a first line extending at a first angle relative to a first normal to the sample at the intersection of said first line and the sample surface to receive optical radiation reflected from said sample;
   a second port disposed in said housing member and directed toward said sample port along a second line extending at a second angle relative to a second normal to the sample at the intersection of said second line and the sample surface to receive optical radiation reflected from said sample concurrently with the reception by said first receiver of optical radiation reflected from said sample surface; and
   wherein each of said first and second ports either is (i) an SCI port which receives optical radiation, including a specular component, reflected from said sample port along the corresponding said first or second line, or is (ii) an SCE port which receives optical radiation reflected from said sample port exclusive of specular component, said first port and said second port respectively selected from the group consisting of:
      a first SCE port and a second SCE port located in opposite relationship to each other;
      a first SCE port and a second SCE port located in non-opposite relationship to each other; and
      a first SCI port and a second SCI port located in non-opposite relationship to each other and each receiving respective specular components from respective portions of the common optically diffuse and highly reflective inner surface.

2. The integrating sphere according to claim 1, wherein said first and second lines intersect the sample surface at a common point.

3. The integrating sphere according to claim 1, wherein said first and second angles are equal.

4. The integrating sphere according to claim 1, wherein said first and second ports respectively are said first SCE port and said second SCE port located in non-opposite relationship to each other, wherein said housing includes a second SCI port disposed opposite to said first SCE port.

5. The integrating sphere according to claim 1, wherein said first and second ports respectively are said first SCE port and said second SCE port located in opposite relationship to each other, wherein said housing includes an SCI port disposed non-opposite to said first SCE port and non-opposite to said second SCE port and directed at said sample port along a third line extending at a third angle relative to a third normal to the sample at the intersection of said third line and the sample surface.

6. The integrating sphere according to claim 1, wherein said first and second ports respectively are said first SCE port and said second SCE port located in opposite relationship relative to each other, wherein said housing includes an SCI port directed toward said sample port along a third line extending at a third angle relative to a third normal to the sample at the intersection of said third line and the sample surface.

7. The integrating sphere according to claim 6, wherein said housing includes an additional SCI port non-oppositely disposed to said SCI port and directed toward said sample port along a fourth line extending at a fourth angle relative to a fourth normal to the sample at the intersection of said fourth line and the sample surface.

8. The integrating sphere according to claim 7, wherein the respective lines along which each of said first and second SCE ports and said SCI and additional SCI ports are directed toward said sample all intersect the sample at a common point.

9. The integrating sphere according to claim 7, wherein each of said angles are equal.

10. The integrating sphere according to claim 1, wherein said first and second ports respectively are said first SCE port and said second SCE port located in opposite relationship to each other, wherein said housing includes a third SCE port directed at said sample along a third line extending at a third angle relative to a third normal to the sample at the intersection of said third line and the sample surface to receive optical radiation reflected from said sample.

11. The integrating sphere according to claim 10, wherein said third angle is unequal to said first and second angles which are equal to each other.

12. The integrating sphere according to claim 1, wherein said first and second ports respectively are said first SCE port and said second SCE port located in non-opposite relationship relative to each other, wherein said housing includes an SCI port.

13. The integrating sphere according to claim 1, wherein said first and second ports respectively are said first SCI port and said second SCI port located in non-opposite relationship to each other, wherein said first and second receivers view different sized area-of-views of said sample.

14. The integrating sphere according to claim 1, wherein said first and second ports respectively are said first SCI port and said second SCI port located in non-opposite relationship relative to each other, wherein said first and second angles are not equal.

15. The integrating sphere according to claim 1, wherein said first and second ports respectively are said first SCI port and said second SCI port located in non-opposite relationship relative to each other, wherein said housing includes an SCE port directed at said sample along a third line extending at a third angle relative to a third normal to the sample at the intersection of said third line and the sample surface to receive optical radiation reflected from said sample.

16. The integrating sphere according to claim 1, wherein said optical radiation source is substantially external to said cavity, and wherein said housing includes an aperture through which optical radiation from said optical radiation source is coupled into said cavity.

17. The integrating sphere according to claim 1, further comprising a baffle that blocks optical radiation from said optical radiation source from directly impinging on the region of said sample port viewed by said first and second ports.

18. The integrating sphere according to claim 1, wherein said first and second ports each have an associated optical receiver.

19. The integrating sphere according to claim 1, wherein said housing includes a reference aperture directed at said inner surface to receive optical radiation diffusely reflected thereby independent of optical radiation directly from said sample port.

20. The integrating sphere according to claim 1, wherein said first and second ports are optically coupled to respective inputs of a spectrophotometer which concurrently detects the optical radiation received by said first and second ports.

21. The integrating sphere according to claim 1, wherein at least one of said first and second ports includes coaxial receivers.

22. An integrating sphere, comprising:
   a housing member having a cavity with an optically diffuse and highly reflective inner surface;
   said housing member including a sample port where a sample is placed;
   an optical radiation source which provides optical radiation directed toward said inner surface to diffusely illuminate said sample port;
   a first port disposed in said housing member and directed toward said sample port along a first line extending at a first angle relative to a first normal to the sample at the intersection of said first line and the sample surface to receive optical radiation reflected from said sample;
   a second port disposed in said housing member and directed toward said sample port along a second line extending at a second angle relative to a second normal to the sample at the intersection of said second line and the sample surface to receive optical radiation reflected from said sample concurrently with the reception by said first receiver of optical radiation reflected from said sample surface; and
   wherein each of said first and second ports is an SCE port which receives optical radiation reflected from said sample port exclusive of specular component, said first port and said second port being located in opposite relationship to each other, wherein said first and second ports view different sized area-of-views of said sample.

23. A spectrophotometer apparatus, comprising:
   an integrating sphere having a cavity with an optically diffuse and highly reflective inner surface;
   said integrating sphere including a sample port where a sample is placed;
   an optical radiation source which provides optical radiation directed toward said inner surface to diffusely illuminate said sample port;
   a first port disposed in said integrating sphere and directed toward said sample port along a first line extending at a first angle relative to a first normal to the sample at the intersection of said first line and the sample surface to receive optical radiation reflected from said sample;
   a second port disposed in said integrating sphere and directed toward said sample port along a second line extending at a second angle relative to a second normal to the sample at the intersection of said second line and the sample surface to receive optical radiation reflected from said sample concurrently with the reception by said first receiver of optical radiation reflected from said sample surface;
   a detector optically coupled to said first and second apertures to sense the optical radiation received by the first and second apertures;
   a processor coupled to said detector, and which analyzes electrical signals representing the optical radiation sensed by said detector; and
   wherein each of said first and second ports either is (i) an SCI port which receives optical radiation, including a specular component, reflected from said sample port along the corresponding said first or second line, or is (ii) an SCE port which receives optical radiation reflected from said sample port exclusive of specular component, said first port and said second port respectively selected from the group consisting of:
a first SCE port and a second SCE port located in opposite relationship to each other;
a first SCE port and a second SCE port located in non-opposite relationship to each other; and
a first SCI port and a second SCI port located in non-opposite relationship to each other and each receiving respective specular components from respective portions of the common optically diffuse and highly reflective inner surface.

24. The spectrophotometer according to claim 23, wherein said detector includes respective photosensitive areas to sense optical radiation received by said first and second ports.

25. The spectrophotometer according to claim 23, wherein said detector is a two-dimensional array detector.

26. The spectrophotometer according to claim 23, wherein said detector simultaneously senses optical radiation received by said first and second ports.

27. The spectrophotometer according to claim 23, wherein said first and second ports respectively are said first SCE port and said second SCE port located in opposite relationship relative to each other, wherein said housing includes an SCI port directed toward said sample port along a third line extending at a third angle relative to a third normal to the sample at the intersection of said third line and the sample surface.

28. The spectrophotometer according to claim 27, wherein said housing includes an additional SCI port non-oppositely disposed to said SCI port and directed toward said sample port along a fourth line extending at a fourth angle relative to a fourth normal to the sample at the intersection of said fourth line and the sample surface.

29. The spectrophotometer according to claim 28, wherein the respective lines along which each of said first and second SCE ports and said SCI and additional SCI ports are directed toward said sample all intersect the sample at a common point.

30. The spectrophotometer according to claim 29, wherein each of said angles are equal.

31. The integrating sphere according to claim 23, wherein at least one of said first and second ports includes coaxial receivers.

32. A spectrophotometer apparatus, comprising:
an integrating sphere having a capity with an optically diffuse and highly reflective inner surface;
said integrating sphere including a sample port where a sample is place;
an optical radiation source which provides optical radiation directed toward said inner surface to diffusely illuminate said sample port;
a first port disposed in said integrating sphere and directed toward said sample port along a first line extending at a first angle relative to a first normal to the sample at the interseciton of said first line and the sample surface to receive optical radiation reflected from said sample;
a second port disposed in said integrating sphere and directed toward said sample port along a second line extending at a second angle relative to a second normal to the sample at the interseection of said second line and the sample surface to receive optical radiation reflected from said sample concurrently with the reception by said first receiver of optical radiation reflected from said sample surface;
a detector optically coupled to said first and second apertures to sense the optical radiation received by the first and second apertures;
a processor coupled to said detector, and which analyzes electrical signals representing the optical radiation sensed by said detector;
wherein each of said first and second ports is an SCE port which receives optical radiation reflected from said sample port exclusive of specular component, said first port and said second port being located in opposite relationship relative to each other;
wherein said housing includes an SCI port directed toward said sample port along a third line extending at a third angle relative to a third normal to the sample at the intersection of said third line and the sample surface, and said housing includes an additional SCI port non-oppositely disposed to said SCI port and directed toward said sample port along a fourth line extending at a fourth angle relative to a fourth normal to the sample at the intersection of said fourth line and the sample surface, said SCI port and additional SCI port each receiving optical radiation, including a specular component, reflected from said sample port along the corresponding said third and fourth lines;
wherein the respective lines along which each of said first and second SCE ports and said SCI and additional SCI ports are directed toward said sample all intersect the sample at a common point, and wherein each of said angles are equal; and
wherein said first SCE port and said second SCE port view different sized area-of-views of said sample from each other, and wherein said SCI port and said additional SCI port view different sized area-of-views of said sample from each other.

33. An integrating sphere, comprising:
a housing member having a cavity with an optically diffuse and highly reflective inner surface;
said housing member including a sample port where a sample is placed;
means for diffusely illuminating said sample port;
first means for receiving optical radiation reflected from said sample along a first line extending at a first angle relative to a first normal to the sample at the intersection of said first line and the sample surface;
second means for receiving, concurrently with the reception of optical radiation by said first means, optical radiation reflected from said sample along a second line extending at a second angle relative to a second normal to the sample at the intersection of said second line and the sample surface; and
wherein each of said first and second means either is (i) an SCI receiving means which receives optical radiation, including a specular component, reflected from said sample port along the corresponding said first or second line, or is (ii) an SCE receiving means which receives optical radiation reflected from said sample port exclusive of specular component, said first means and said second means respectively selected from the group consisting of:
a first SCE receiving means and a second SCE receiving means located in opposite relationship to each other;
a first SCE receiving means and a second SCE receiving means located in non-opposite relationship to each other; and
a first SCI receiving means and a second SCI receiving means located in non-opposite relationship to each other and each receiving respective specular components from respective portions of the common optically diffuse and highly reflective inner surface.

34. An integrating sphere, comprising:
a housing member having a cavity with an optically diffuse and highly reflective inner surface;
said housing member including a sample port where a sample is placed;
an optical radiation source which provides optical radiation directed toward said inner surface to diffusely illuminate said sample port;
a first port disposed in said housing member and directed toward said sample port along a first line extending at a first angle relative to a first normal to the sample at the intersection of said first line and the sample surface to receive optical radiation reflected from said sample;
a second port disposed in said housing member and directed toward said sample port along a second line extending at a second angle relative to a second normal to the sample at the intersection of said second line and the sample surface to receive optical radiation reflected from said sample concurrently with the reception by said first receiver of optical radiation reflected from said sample surface; and
wherein each of said first and second ports either is (i) an SCI port which receives optical radiation, including a specular component, reflected from said sample port along the corresponding said first or second line, or is (ii) an SCE port which receives optical radiation reflected from said sample port exclusive of specular component, said first port and said second port respectively selected from the group consisting of:
an SCI port and an SCE port azimuthally displaced by an angle not equal to about pi radians, the SCI port located opposite to said SCE port;
an SCI port and an SCE port azimuthally displaced by an angle equal to about pi radians, the SCI port located opposite to said SCE port, said first angle not equal to said second angle;
an SCI port and an SCE port azimuthally displaced by an angle equal to about pi radians, the SCI port located opposite to said SCE port, said SCI port and said SCE port viewing respective non-overlapping regions of said sample;
a first SCE port and a second SCE port located opposite to said first SCE port;
a first SCE port and a second SCE port located in non-opposite relationship to each other; and
a first SCI port and a second SCI port located in non-opposite relationship to each other and each receiving respective specular components from respective portions of the common optically diffuse and highly reflective inner surface.

35. The integrating sphere according to claim 34, wherein said first and second ports are said SCI port and said SCE port azimuthally displaced by an angle not equal to pi radians, the SCI port located opposite to said SCE port, and wherein said first and second angles are any arbitrary combination of angles, including angles having equal values.

36. The integrating sphere according to claim 34, wherein said first and second ports are said first SCE port and said second SCE port located opposite to said first SCE port, and wherein said first SCE port is opposite to said second SCE port.

37. The integrating sphere according to claim 34, wherein said first and second ports are said first SCE port and said second SCE port located opposite to said first SCE port, and wherein said first and second SCE ports are azimuthally displaced by an angle not equal to about pi radians.

38. The integrating sphere according to claim 34, wherein said first and second ports are said first SCE port and said second SCE port located opposite to said first SCE port, and wherein said first and second SCE ports are azimuthally displaced by an angle equal to about pi radians and said first angle is not equal to said second angle.

39. The integrating sphere according to claim 34, wherein said first and second ports are said first SCE port and said second SCE port located opposite to said first SCE port, and wherein said first and second SCE ports are azimuthally displaced by an angle equal to about pi radians, said first and second SCE ports viewing respective non-overlapping regions of said sample.

40. The integrating sphere according to claim 34, wherein at least one of said first and second ports includes coaxial receivers.

41. In a spectrophotometer, a method of measuring optical radiation reflected from a sample under test, the method comprising the steps of:
exposing a selected surface area of said sample under test to diffused optical radiation;
sensing first optical radiation reflected from said sample along a first line extending at a first angle relative to a first normal to the sample at the intersection of said first line and the sample surface;
sensing, concurrently with the step of sensing said first optical radiation, second optical radiation reflected from said sample along a second line extending at a second angle relative to a second normal to the sample at the intersection of said second line and the sample surface; and
wherein each of said first and second optical radiation either includes a specular component reflected from said sample under test along the corresponding said first or second line, or excludes any specular components, corresponding to respective ports for including or excluding specular optical radiation, respectively designated SCI port and SCE port, and selected from the group consisting of:
a first SCE port and a second SCE port located in opposite relationship to each other;
a first SCE port and a second SCE port located in non-opposite relationship to each other; and
a first SCI port and a second SCI port located in non-opposite relationship to each other and each receiving respective specular components from respective portions of the common optically diffuse and highly reflective inner surface.

* * * * *